United States Patent [19]

Manada et al.

[11] Patent Number: 5,403,949
[45] Date of Patent: Apr. 4, 1995

[54] METHOD OF PRODUCING CARBONIC ACID DIESTER

[75] Inventors: Noriaki Manada; Masato Murakami; Koji Abe; Yasushi Yamamoto; Toshio Kurafuji, all of Ube, Japan

[73] Assignee: Ube Industries, Ltd., Yamaguchi, Japan

[21] Appl. No.: 99,724

[22] Filed: Jul. 29, 1993

[30] Foreign Application Priority Data

Jul. 31, 1992 [JP] Japan .................. 4-245412
May 11, 1993 [JP] Japan .................. 5-109348

[51] Int. Cl.$^6$ .................................. C07C 69/96
[52] U.S. Cl. .................................. 558/277; 558/260
[58] Field of Search .................................. 558/277

[56] References Cited

U.S. PATENT DOCUMENTS

| | | | |
|---|---|---|---|
| 4,318,862 | 3/1982 | Romano et al. | 260/463 |
| 5,089,650 | 2/1992 | Yokota et al. | 558/277 |
| 5,128,306 | 7/1992 | Dettling et al. | 502/304 |
| 5,162,563 | 11/1992 | Nishihira et al. | 558/260 |
| 5,214,184 | 5/1993 | Matuzaki et al. | 558/277 |
| 5,214,185 | 5/1993 | Nishihira et al. | 558/277 |
| 5,231,213 | 6/1993 | Landscheidt et al. | 558/277 |
| 5,292,916 | 3/1994 | Matsuzaki et al. | 558/275 |

FOREIGN PATENT DOCUMENTS

| | | |
|---|---|---|
| 0425197 | 10/1990 | European Pat. Off. . |
| 0501507 | 2/1992 | European Pat. Off. . |
| 0503091 | 9/1992 | European Pat. Off. . |
| 60-75447 | 4/1985 | Japan . |
| 60-181050 | 9/1985 | Japan . |
| 63-72650 | 4/1988 | Japan . |
| 3141243 | 6/1991 | Japan . |
| 489458 | 3/1992 | Japan . |
| 4139152 | 5/1992 | Japan . |

*Primary Examiner*—José G. Dees
*Assistant Examiner*—Barbara S. Frazier
*Attorney, Agent, or Firm*—Burgess, Ryan & Wayne

[57] ABSTRACT

A carbonic acid diester is produced, at a high reaction rate with a high selectivity and stability, by catalytically reacting carbon monoxide with a nitrous acid ester, preferably in a gas phase, in the presence of a solid catalyst composed of a solid carrier and a catalytic solid material deposited on the carrier and comprising:

(1) a first catalyst component comprising at least one member selected from the group consisting of platinum group metals and compounds thereof;

(2) a second catalyst component comprising at least one member selected from the group consisting of lanthanide group metals and compounds thereof; and collecting the resultant carbonic acid diester from a reaction mixture discharged from the catalytic reaction step.

18 Claims, No Drawings

METHOD OF PRODUCING CARBONIC ACID DIESTER

BACKGROUND OF THE INVENTION

1. Field of the Invention

The present invention relates to a method of producing a carbonic acid diester.

More particularly, the present invention relates to a process of continuously producing a carbonic acid diester from carbon monoxide and a nitrous acid ester by using a new type of catalyst having a high selectivity, at a high reaction rate with a high selectivity and stability over a long period of time.

The carbonic acid diester is very useful as a starting material of medicines and pesticides, and as an intermediate compound of a polycarbonate and urethane.

2. Description of the Related Art

A conventional method of producing a carbonic acid diester by a reaction of phosgene with an alcohol is well known, and has been practiced for some time. Nevertheless, this conventional method is disadvantageous in that phosgene has an extremely strong toxicity, and thus, is not preferable as a starting material in view of environmental and health considerations. Also, the reaction of phosgene with an alcohol produces hydrochloric acid as a by-product, which corrodes the reaction device.

Therefore, there is a strong demand for a new method of producing a carbonic acid diester without using phosgene.

In response to this demand, various attempts have been made to produce a carbonic acid diester from an alcohol and carbon monoxide, as disclosed in, for example, Japanese Unexamined Patent Publication (Kokai, JP-A) No. 60-75,447, and 63-72,650, and Japanese Examined Patent Publication (Kokoku, JP-B) 63-38,018.

In those methods, the carbonic acid diester is produced by a catalytic oxygen-oxidizing reaction of carbon monoxide with an alcohol in a liquid phase, in the presence of a catalyst consisting of a copper halide or palladium halide.

These methods are disadvantageous in that, in the catalytic oxygen-oxidizing reaction, carbon dioxide is produced as a by-product, and thus the production of the carbonic acid diester is effected with a low selectivity based on the amount of carbon monoxide supplied to the reaction system. Also, the catalytic oxygen-oxidizing reaction produces water ($H_2O$) as another by-product, and thus the resultant carbonic acid diester must be isolated from the water by a difficult refining procedure. Also, the above-mentioned methods are further disadvantageous in that since the reaction is carried out in a liquid phase, the resultant carbonic acid diester must be separated from the catalyst in the reaction system.

Accordingly, the above-mentioned methods are not satisfactory for industrial use.

There have been attempts made to eliminate the above-mentioned disadvantages, and as one such attempt, Japanese Unexamined Patent Publication No. 60-181,051 discloses a method of producing carbonic acid diester by a catalytic oxidizing reaction of a nitrous acid ester with carbon monoxide, in a gas phase, in the presence of a catalyst composed of a solid platinum group metal or compound thereof carried on a solid carrier and an oxidant in an amount of 10 molar % in terms of $O_2$, per mole of carbon monoxide present in the reaction mixture.

In this method, the oxidant in the above-mentioned specific amount based on the carbon monoxide effectively inhibits a production of oxalic acid diester as a by-product, but the addition of the oxidant in the above-mentioned specific acid based on the amount of the carbon monoxide cannot completely inhibit the production of the oxalic acid diester, and therefore, the desired carbonic acid diester is produced with an unsatisfactorily low selectivity. Also the reaction rate and the durability of the catalyst are unsatisfactory.

Further, the above-mentioned method is further disadvantageous in that the proportion of nitrous acid ester in a reaction mixed gas comprising the nitrous acid ester, carbon monoxide, alcohol and oxygen is higher than an explosion (flammable) limit of the mixed gas, and thus this reaction mixed gas is not preferable in view of the safety of the procedure.

Accordingly this method is not satisfactory for practical use.

Japanese Unexamined Patent Publication Nos. 3-141,243 and 4-139,152 disclose a method of producing dimethyl carbonate by a catalytic reaction of carbon monoxide with methyl nitrite in a gas phase by using a catalyst comprising a carrier, for example, activated carbon, and a catalytic member selected from compounds of platinum group metals, for example, palladium chloride and palladium sulfate, and compounds of metals selected from iron, copper, bismuth, cobalt, nickel and tin, and carried on the carrier. This method is unsatisfactory in catalytic activity and durability of the catalyst for practical use.

Japanese Unexamined Patent Publication No. 4-89,458 discloses a method of producing dimethyl carbonate by a catalytic reaction of carbon monoxide with methyl nitrite in a gas phase, in the presence of a catalyst comprising a carrier consisting of, for example, activated carbon, and a catalytic member selected from compounds of platinum group metals, for example, palladium chloride and palladium sulfate, and compounds of specific metals selected from iron, copper, bismuth, cobalt, nickel and tin, and further in the presence of a small amount of hydrogen chloride, while maintaining the catalytic activity of the catalyst at a high level over a long period of time. However, the practical life span of the catalyst is not always satisfactory, and thus there is a demand for an improved method satisfactory for practical use.

As mentioned above, the conventional methods of producing carbonic acid diester from nitrous acid ester and carbon monoxide are unsatisfactory in the durability of the catalyst and are not always satisfactory in reaction rate and selectivity.

SUMMARY OF THE INVENTION

An object of the present invention is to provide a method of producing a carbonic acid diester from a nitrous acid ester and carbon monoxide by a catalytic reaction procedure, by which the resultant carbonic acid diester can be easily isolated and recovered.

Another object of the present invention is to provide a method of producing a carbonic acid diester from a nitrous acid ester and carbon monoxide in the presence of a catalyst having a high resistance to deterioration and deactivation and thus usable stably over a long period of time.

Still another object of the present invention is to provide a method of producing a carbonic acid diester by a catalytic reaction of a nitrous acid ester with carbon monoxide under moderate and safe reaction conditions, at a high reaction rate with a high selectivity and stability.

The above-mentioned objects can be attained by the method of the present invention for producing a carbonic acid diester, which comprises the steps of:

(A) catalytically reacting carbon monoxide with a nitrous acid ester in the presence of a solid catalyst composed of a solid carrier and a catalytic solid material carried on the carrier and comprising:
  (1) a first catalyst component comprising at least one member selected from the group consisting of platinum group metals and compounds thereof;
  (2) a second catalyst component comprising at least one member selected from the group consisting of lanthanide group metals and compounds thereof; and
(B) collecting the resultant carbonic acid diester from a reaction mixture discharged from the catalytic reaction step (A).

In the method of the present invention, the catalytic solid material optionally further comprises at least one additional component selected from the group consisting of iron, copper, bismuth, cobalt, nickel, tin, vanadium, molybdenum and tungsten, and compounds of the above-mentioned metals.

DESCRIPTION OF THE PREFERRED EMBODIMENTS

In the method of the present invention, a nitrous acid ester is reacted with carbon monoxide in the presence of a specific solid catalyst to produce a carbon acid diester at a high reaction rate with a high selectivity and stability. Preferably, the catalytic reaction is carried out in a gas phase.

The nitrous acid ester usable for the method of the present invention is preferably selected from the group consisting of nitrites of lower aliphatic monohydric alcohols having 1 to 4 carbon atoms, for example, methyl nitrite, ethyl nitrite, n-propyl nitrite, isopropyl nitrite, n-butyl nitrite, isobutyl nitrite and sec-butyl nitrite; nitrites of cycloaliphatic monohydric alcohols, for example, cyclohexyl nitrite; and nitrites of aralkyl monohydric alcohols, for example, benzyl nitrite and phenylethyl nitrite.

Among the above-mentioned nitrous acid esters, the nitrites of aliphatic monohydric alcohols having 1 to 4 carbon atoms are preferable for the present invention, and the most preferable nitrous acid esters for the present invention are methyl nitrite and ethyl nitrite.

The solid catalyst usable for the present invention comprises a solid carrier and a catalytically active solid material carried on the solid carrier.

The catalytic solid material comprises:
  (1) a first catalyst component consisting of at least one member selected from the group consisting of platinum group metals, for example, palladium, platinum, iridium, ruthenium and rhodium, and compounds of the platinum group metals, preferably platinum group metal compounds; and
  (2) a second catalyst component consisting of at least one member selected from the group consisting of lanthanide group metals and compounds thereof.

The platinum group metal compounds usable for the first catalyst component include halides, for example, chlorides, bromides, iodides and fluorides, inorganic acid salts, for example, nitrates, sulfates, and phosphates, and organic acid salts, for example, acetates, and benzoates of the platinum group metals.

The platinum group compounds preferably selected from the group consisting of halides, for example, palladium chloride, palladium bromide, palladium iodide, palladium fluoride, lithium tetrachloropalladate, sodium tetrachloropalladate, potassium tetrachloropalladate, platinum chloride, iridium chloride, ruthenium chloride, ruthenium bromide, rhodium chloride, rhodium bromide, and rhodium iodide; inorganic acid salts, for example, palladium nitrate, palladium sulfate, palladium phosphate, rhodium nitrate and rhodium sulfate; and organic acid salts, for example, palladium acetate, palladium benzoate and rhodium acetate.

Among the above-mentioned compounds, the halides and sulfates of palladium, ruthenium and rhodium are particularly preferable for the present invention, but the most preferable compound for the first catalyst component is palladium chloride.

The chlorides of the platinum group metals usable for the present invention are not limited to those as mentioned above. The substances usable for the first catalyst component may be platinum group metals or the compound of the metals, which are capable of producing complexes contributory to the reaction of the above-mentioned chlorides or chlorine in the presence of hydrogen chloride.

In the second catalyst component (2) of the present invention the lanthanide group metal is selected from the group consisting of lanthanum, cerium, praseodymium, neodymium, promethium, samarium, europium, gadolinium terbium dysprosium, holmium, erbium, thulium, ytterbium, and lutetium.

Also, the lanthanide group metal compound is selected from the group consisting of oxides, halides, and inorganic and organic salts of the lanthanide group metals.

Preferably, the lanthanide group metal compound is selected from oxides, chlorides and nitrates of the lanthaide group metal.

Optionally, the catalytic solid material usable for the present invention further comprises at least one additional component selected from the group consisting of iron, copper, bismuth, cobalt, nickel, tin, vanadium, molybdenum, tungsten, and compounds of the above-mentioned metals.

The compounds of iron, copper, bismuth, cobalt, nickel, and tin are halides, for example, chlorides, bromides iodides and fluorides inorganic acid salts, for example, nitrates, sulfates and phosphates, and organic acid salts, for example, acetates, of the above-mentioned metals.

Preferably, the metal compounds usable for the additional catalyst component are selected from iron, copper, bismuth, cobalt, nickel, tin, halides and sulfates of the above-mentioned metals.

The compounds of vanadium, molybdenum, and tungsten are oxides, metal acids, metal salts of the metal acids and ammonium salts of the metal acids of the above-mentioned metals.

The vanadium, molybdenum and tungsten compounds usable for the additional catalyst components may be selected from metal oxides, namely vanadium oxide, molybdenum oxide, and tungsten oxide; and metal acid ammonium salts, for example, ammonium vanadate, ammonium molybdate and ammonium tungstate.

The solid carrier usable for the method of the present invention preferably comprises at least one member selected from the group consisting of diatomaceous earth, activated carbon, silicon carbide, titania, zeolite, alumina, for example, γ-alumina, and silica-alumina. The activated carbon, zeolite, alumina, and silica-alumina are the most preferable materials for the solid carrier.

The catalytically active solid material can be carried on the solid deposited by a conventional application method, for example, an impregnating immersion-absorption method in which the solid carrier is immersed in a dispersion of the catalytic solid material in the form of fine particles, so that the catalytic solid material particles are allowed to be adsorbed by the solid carrier, a mix-kneading method in which a mixture of grains of the solid carrier and fine particles of the catalytic solid material is kneaded so that the catalytic solid material particles are adhered to the solid carrier grains, a deposition method in which fine particles of the catalytic solid particles are deposited on the solid carrier grains, an evaporate-drying method in which a dispersion of the catalytic solid material in a volatile solvent is applied to solid carrier grains and then the resultant product is dried by evaporating away the volatile solvent, or a co-precipitation method in which the solid carrier and the catalytic solid material are co-precipitated from a solution thereof so that the precipitated catalytic solid material in the form of fine particles is carried on the precipitated solid carrier in the form of grains or particles.

Preferably, in the preparation of the solid catalyst of the present invention, the impregnating method and the evaporate-drying method are utilized, because these methods are simple and easy.

These methods are carried out by using a solvent. The solvent is preferably selected from for example, aqueous hydrochloric acid solution, aqueous ammonia solution and alcohols, which are capable of dissolving uniformly the above-mentioned catalyst components.

In the preparation of the solid catalyst, the catalyst components may be carried at one time or successively stepwise.

In the solid catalyst of the present invention, the first catalyst component is preferably present in an amount, in terms of the platinum group metal as used, of 0.1% to 10% by weight, more preferably 0.5% to 2% by weight, based on the weight of the solid carrier.

Also, the second catalyst component (lanthanide group metals or compounds thereof) preferably present in an amount, in terms of the lanthanide group metal as used, of 0.1 to 50 gram atom equivalents, more preferably to 10 gram atom equivalents, per gram atom equivalent of the first catalyst component in terms of the platinum group metal contained therein.

Further, the additional catalyst component comprising at least one member selected from iron, copper, bismuth, cobalt, nickel, tin and compounds thereof is preferably present in an amount, in terms of the metal as used, of 0.1 to 50 gram atom equivalents, more preferably 1 to 10 gram atom equivalents, per gram atom equivalent of the first catalyst component in terms of the platinum group metal contained therein.

Furthermore, the additional catalyst component comprising at least one member selected from vanadium, molybdenum, tungsten and compounds thereof is preferably present in an amount, in terms of the metal as used, of 0.1 to 20 gram atom equivalent, more preferably 0.5 to 10 gram atom equivalent, per gram atom equivalent of the first catalyst component in terms of the platinum group metal contained therein.

Usually, the solid catalyst usable for the present invention is in the form of fine particles, coarse particles, grains or other shapes. There is no limitation of the size of the solid catalyst.

Preferably, the solid catalyst in the form of fine particles has a size of from 20 to 100 μm.

Also, the solid catalyst in the form of coarse particles preferably has a mesh size of from 4 to 200.

Further, the solid catalyst in the form of grains or shaped articles preferably has a size of 0.5 to 10 mm.

The catalytic reaction step of the nitrous acid ester with carbon monoxide can be carried out in a batch system or a continuous reaction system in a gas phase or a liquid phase. The continuous reaction system in a gas phase is advantageous for an industrial production of the carbonic acid diester.

In any reaction system, the solid catalyst of the present invention may be placed in a fixed catalyst bed or a fluidized catalyst bed of a reactor.

When the specific solid catalyst of the present invention is employed, the catalytic reaction of a nitrous acid ester with carbon monoxide can be effectively conducted even under moderate conditions. For example, the catalytic reaction in the method of the present invention can be effected at a temperature of from 0° C. to 200° C., preferably from 50° C. to 140° C. under the ambient atmospheric pressure. Of course, the catalytic reaction of the present invention can be effected under pressurized conditions, without difficulty. For example, the catalytic reaction of the present invention can be carried out at a temperature of 50° to 150° C. under a pressure of 1° to 20 kg/cm$^2$G.

The nitrous acid ester usable as a starting substance for the method of the present invention can be easily prepared, for example, by decomposing sodium nitrite in an aqueous solution in the presence of nitric acid or sulfuric acid to generate a mixed gas of nitrogen monoxide (NO) and nitrogen dioxide (NO$_2$), oxidizing a portion of the nitrogen monoxide (NO) in the mixed gas with molecular oxygen to convert same to nitrogen dioxide (NO$_2$) and to provide a NOx gas having a molar ratio of nitrogen monoxide to nitrogen dioxide, NO/NO$_2$, of 1/1, and bringing the NOx gas into contact with an alcohol.

In another method, after the catalytic reaction is completed, a reaction gas is discharged from the reactor, nitrogen monoxide (NO) generated from the nitrous acid ester is separated from the discharged reaction gas, and then reacted with oxygen and the corresponding alcohol to re-produce a nitrous acid ester.

In the above-mentioned methods, the nitrous acid ester-preparation step and the carbon monoxide-nitrous acid ester reaction step are preferably carried out in a slightly pressurized system, for example, under a pressure of about 2 to 3 kg/cm$^2$.

The nitrous acid ester-containing gas prepared by the above-mentioned methods, contains, in addition to the nitrous acid ester, unreacted alcohol, nitrogen oxides (particularly NO), and occasionally a small amount of water and/or oxygen. This type of nitrous acid ester-containing gas can be employed as a nitrous acid ester source and a good result can be obtained.

In the method of the present invention, the starting materials, i.e., carbon monoxide and a nitrous acid ester, are fed in a gas phase into a reactor. In this feed gas, the starting materials are preferably diluted with an inert gas, for example, a nitrogen, argon or carbon dioxide gas.

The feed gas for the catalytical reaction step need not have a specific composition, but from the viewpoint of safety, the feed gas preferably has a content of the nitrous acid ester of 20% by volume or less, more preferably, 5 to 20% by volume. Also, from the viewpoint of economy, the content of carbon monoxide in the feed gas is from 5% to 20% by volume.

When the nitrous acid ester is diluted with carbon monoxide in place of the inert gas, and the resultant feed gas is fed into a reactor, the content of carbon monoxide in the feed gas is allowed to be raised up to 80% by volume. Nevertheless, in an industrial production process, it is preferable that the feed gas to be subjected to the reaction be returned to the reaction step for reuse by discharging a portion of the returned gas to the outside of the reaction system. Also, usually, carbon monoxide is consumed at a conversion of about 20% to 30% by volume per one pass through the reaction system. Therefore, a content of carbon monoxide of more than 20% by volume in the feed gas does not bring any advantage but results in an increased loss thereof.

Also, a content of carbon monoxide of less than 5% by volume brings an unsatisfactory productivity of a carbonic acid diester. Accordingly, from the view point of economy, the content of carbon monoxide in the feed gas is preferably in the range of from 5% to 20% by volume.

In the method of the present invention, the feed gas preferably contains carbon monoxide in a molar ratio to a nitrous acid ester of 0.1/1 to 10/1, more preferably 0.25/1 to 1/1. Also, the feed gas is preferably fed into a catalytic reaction step (reactor) at a space velocity of 500 to 20,000 $hr^{-1}$, more preferably 2,000 to 15,000 $hr^{-1}$.

In the method of the present invention, it is preferable that a reduction in catalytic activity of the catalyst be prevented by carrying out the catalytic reaction of carbon monoxide with a nitrous acid ester in the presence of a catalytic activity reduction-inhibiting agent comprising at least one member selected from the group consisting of hydrogen chloride and chloroformic acid esters.

In this method, hydrogen chloride is preferably anhydrous, and the chloroformic acid esters are preferably selected from the group consisting of esters of chloroformic acid with a lower aliphatic monohydric alcohols, for example, methyl chloroformate, ethyl chloroformate, n-propyl chloroformate, isopropyl chloroformate, n-butyl chloroformate, isobutyl chloroformate and sec-butyl chloroformate; esters of chloroformic acid with cycloaliphatic alcohols, for example, cyclohexyl chloroformate, and esters of chloroformic acid with aralkyl alcohols, for example, phenylethyl chloroformate. Usually, a chloroformic acid ester having the same alkoxyl group as in the nitrous acid ester used is preferably employed.

There is no restriction to a manner in which hydrogen chloride or a chloroformic acid ester is incorporated into the reaction system. For example, a small amount of hydrogen chloride or a chloroformic acid ester is continuously added to the reaction system in the following manner.

When hydrogen chloride is continuously added, if the amount of hydrogen chloride is too large, the hydrogen chloride is adsorbed by the catalyst and the catalytic reaction is hindered. Therefore, the amount of hydrogen chloride to be added to the reaction system is preferably controlled to a specific level of 1 to 50 molar %, more preferably 5 to 20 molar %, based on the molar amount of the platinum group metal in the catalyst, per unit time. Particularly, where the catalytic reaction is carried out in a fixed bed type reactor at a gas phase space velocity (GHSV) of 3,000 $hr^{-1}$, hydrogen chloride is preferably added in an amount of 5 to 500 ppm by volume, more preferably 10 to 100 ppm by volume into the feed gas and the hydrogen chloride-containing feed gas is continuously fed into the reactor.

When a chloroformic acid ester is continuously added to the reaction system, there is no upper limit to the amount of the chloroformic acid ester. However, the use of chloroformic acid ester in a too large an amount is economically disadvantageous. It is preferable that the chloroformic acid ester be added in an amount of 1% by volume or less, more preferably 1000 ppm by volume or less to the feed gas, and the chloroformic acid ester-containing feed gas be fed continuously into the reactor.

The addition of the chloroformic acid ester to the feed gas can be carried out in one of the following manners.

In one manner, a nitrogen gas flows on a surface of a heated chloroformic acid ester to allow a vapor generated from the heated chloroformic acid ester to be incorporated into the nitrogen gas stream.

In another manner, a reactor equipped with an inlet conduit for feeding a feed gas and another inlet conduit for feeding a chloroformic acid ester-containing gas is used. The chloroformic acid ester is evaporated in an evaporator arranged outside of the reactor, and the resultant chloroformic acid ester vapor is fed together with a carrier gas consisting of, for example, nitrogen gas, into the reactor through the above-mentioned other inlet conduit.

Other manners usable for industrial procedures can be utilized for this purpose.

When the catalytic reaction is completed, a resultant reaction gas (mixture) is discharged from the reactor. The resultant reaction gas comprises, in addition to the desired carbonic acid diester corresponding to the nitrous acid ester used, by-products, for example, oxalic acid diester, unreacted carbon monoxide and nitrous acid ester, another by-products, for example, nitrogen monoxide and carbon dioxide.

The discharged reaction mixture is subjected to a cool-condensing procedure, a non-condensed gas fraction comprising carbon monoxide, nitrous acid ester, nitrogen monoxide and carbon dioxide is purged from the reaction mixture, and returned to the reactor. The resultant carbonic acid diester is easily separated from the reaction mixture and collected by a customary method, for example, distillation.

The carbonic acid diesters capable of being produced by the method of the present invention include dialkyl carbonates, for example, dimethyl carbonate, diethyl carbonate, and di-n-propyl carbonate; dicycloalkyl carbonates, for example, dicyclohexyl carbonate; and diaralkyl carbonates, for example, dibenzyl carbonate. Preferably, the method of the present invention is utilized to produce di-lower alkyl carbonates, for example, dimethyl carbonate.

The present invention will be further illustrated by way of specific examples which are merely representative and do not restrict the scope of the present invention in any way.

In the examples, the space time yield (STY) in g/liter·hr of the resultant product was calculated in accordance with the following equation (I):

$$STY (g/liter \cdot hr) = a(b \times \theta) \quad (I)$$

wherein $\theta$ represents a catalytic reaction time in hours of carbon monoxide with a nitrous acid ester in a reaction tube, a represents a weight in grams of the resultant carbonic acid diester during the catalytic reaction time $\theta$, and b represents a volume in liters of a solid catalyst present in the reaction tube.

Also, in the examples, the selectivity X of the carbonic acid diester (for example, dimethyl carbonate) based on carbon monoxide, and the electivity Y of the carboxylic acid diester based on a nitrous acid ester were calculated in accordance with the following equations (II) and (III):

$$X(\%) = \{C/(c + 2 \times d + e)\} \times 100 \quad (II)$$

and $$Y(\%) = \{C/(c + d + f + g)\} \times 100 \quad (III)$$

wherein X and Y are as defined above, c, d, e, f, and g respectively represent the amounts in moles of a carbonic acid diester, an oxalic acid diester, carbon dioxide, formic acid ester and dialkylformal (for example, methylal), each produced within the reaction time $\theta$ in hours, under the given reaction conditions.

c . . . carbonic acid diester
d . . . oxalic acid diester
e . . . carbon dioxide
f . . . formic acid ester
g . . . dialkylformal

Example 1

Preparation of Catalyst

A catalyst component solution containing Pd, Cu and Ce was prepared by heat-dissolving 0.178 g (1 millimole) of palladium chloride ($PdCl_2$), 0.340 g (2 millimoles) of cupric chloride ($CuCl_2 \cdot 2H_2O$) and 0.746 g (2 millimoles) of cerium chloride hexahydrate ($CeCl_3 \cdot 6H_2O$) in 40 ml of methyl alcohol at a temperature of 40° C. to 50° C.

Granular activated carbon in an amount of 10 g was immersed in the solution, and the resultant mixture was stirred at room temperature for one hour. Then, methyl alcohol was evaporated away from the mixture at a temperature of 50° C. under a reduced pressure. The resultant mixture was dried in a nitrogen gas atmosphere at a temperature of 200° C, to provide a solid catalyst. In the resultant catalyst, a mixture of $PdCl_2$, $CuCl_2$ and $CeCl_3$ was carried on a carrier consisting of the activated carbon. The total content of the metal compound in terms of metallic palladium was 1.0% by weight based on the weight of the carrier, and the atomic ratio of Pd, Cu and Ce in the catalyst was Pd:Cu:Ce = 1:2:2.

Production of a Carbonic Acid Diester

The above-mentioned solid catalyst in an amount of 1.5 ml was placed in a gas phase reaction tube having an inside diameter of 20 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 120° C.

A mixed gas consisting of 8% by volume of methyl nitrite, 8% by volume of carbon monoxide, 3% by volume of nitrogen monoxide, 10% by volume of methyl alcohol and 71% by volume of nitrogen was fed into the reaction tube through a top inlet thereof at a space velocity (GHSV) of 8,000 $hr^{-1}$ under the ambient atmospheric pressure. The methyl nitrite was produced from nitrogen monoxide, oxygen and methyl alcohol.

In the reaction tube, the methyl nitrite reacted with carbon monoxide at a temperature of 120° C. in the presence of the solid catalyst.

The resultant reaction mixture discharged from the reaction tube through a bottom thereof was made to flow through methyl alcohol cooled with ice, to collect the resultant reaction product. The collected reaction product was subjected to gas chromatography, and it was confirmed that at 4 hours after the start of the reaction procedure, the space time yield (STY) of dimethyl carbonate was 475 g/liter·hr.

The selectivities (X and Y) of dimethyl carbonate based on carbon monoxide and on methyl nitrite were 95% and 97%, respectively.

Comparative Example 1

Preparation of Catalyst

A catalyst was prepared by the same procedures as in Example 1, except that no cerium chloride hexahydrate ($CeCl_3 \cdot 6H_2O$) was used. In the resultant catalyst, a catalyst solid mixture of $PdCl_2$ and $CuCl_2$ was carried on a carrier consisting of the activated carbon, the total amount of the metal compounds was 1% by weight in terms of metallic Pd, based on the weight of the carrier and the atomic ratio of Pd to Cu was Pd:Cu = 1:2.

Preparation of Dimethyl Carbonate

Dimethyl carbonate was produced by the same procedures as in Example 1 except that the above-mentioned catalyst was employed for the catalyst of Example 1. As a result, it was confirmed that the STY of dimethyl carbonate was 494 g/liter·hr and the selectivities X and Y of dimethyl carbonate based on carbon monoxide and on methyl nitrite were 88% and 89%, respectively.

Examples 2 to 17 and Comparative Example 2

Preparation of Catalyst

In each of Examples 2 to 17 and Comparative Example 2, a catalyst was produced by the same procedures as in Example 1, except that the catalyst was prepared from the platinum group metal compound, lanthanide group metal compound and at least one member selected from iron, copper, bismuth, cobalt, nickel, tin, vanadium, molybdenum and tungsten compounds, in the composition, atomic ratio and amount as shown in Table 1.

Preparation of Dimethyl Carbonate

Dimethyl carbonate was prepared by the same procedures as in Example 1, except that the above-mentioned catalyst was employed in place of the catalyst of Example 1. The results are shown in Table 1.

TABLE 1

| Example No. | Composition of catalyst Metal compounds/carrier(*)₁ | Metal atomic ratio | Space time yield (STY) (g/liter · hr) | Selectivity of dimethyl carbonate (%) Based on CO [X] | Selectivity of dimethyl carbonate (%) Based on methyl nitrite [Y] |
|---|---|---|---|---|---|
| Example 1 | $PdCl_2$—$CeCl_3$—$CuCl_2$/C | Pd/Ce/Cu = 1:2:2 | 475 | 95 | 97 |
| Comparative Example 1 | $PdCl_2$—$CuCl_2$/C | Pd/Cu = 1:2 | 494 | 88 | 89 |
| Example 2 | $PdCl_2$—$LaCl_3$—$CuCl_2$/C | Pd/La/Cu = 1:2:2 | 447 | 95 | 97 |
| 3 | $PdCl_2$—$PrCl_3$—$CuCl_2$/C | Pd/Pr/Cu = 1:2:2 | 471 | 95 | 97 |
| 4 | $PdCl_2$—$NdCl_3$—$CuCl_2$/C | Pd/Nd/Cu = 1:2:2 | 436 | 93 | 96 |
| 5 | $PdCl_2$—$SmCl_3$—$CuCl_2$/C | Pd/Sm/Cu = 1:2:2 | 475 | 93 | 96 |
| 6 | $PdCl_2$—$EuCl_3$—$CuCl_2$/C | Pd/Eu/Cu = 1:2:2 | 422 | 91 | 95 |
| 7 | $PdCl_2$—$GdCl_3$—$CuCl_2$/C | Pd/Gd/Cu = 1:2:2 | 431 | 94 | 97 |
| 8 | $PdCl_2$—$TbCl_3$—$CuCl_2$/C | Pd/Tb/Cu = 1:2:2 | 447 | 92 | 95 |
| 9 | $PdCl_2$—$DyCl_3$—$CuCl_2$/C | Pd/Dy/Cu = 1:2:2 | 413 | 94 | 97 |
| 10 | $PdCl_2$—$HoCl_3$—$CuCl_2$/C | Pd/Ho/Cu = 1:2:2 | 438 | 90 | 94 |
| 11 | $PdCl_2$—$ErCl_3$—$CuCl_2$/C | Pd/Er/Cu = 1:2:2 | 359 | 94 | 97 |
| 12 | $PdCl_2$—$TmCl_3$—$CuCl_2$/C | Pd/Tm/Cu = 1:2:2 | 396 | 90 | 95 |
| 13 | $PdCl_2$—$LaNO_3$—$CuCl_2$/C | Pd/La/Cu = 1:2:4 | 532 | 92 | 93 |
| 14 | $PdCl_2$—$CeCl_3$/C | Pd/Ce = 1:2 | 338 | 98 | 96 |
| 15 | $PdCl_2$—$PrCl_3$/C | Pd/Pr = 1:2 | 302 | 91 | 92 |
| 16 | $PdCl_2$—$EuCl_3$/C | Pd/Eu = 1:2 | 282 | 93 | 93 |
| 17 | $PdCl_2$—$GdCl_3$/C | Pd/Gd = 1:2 | 308 | 92 | 91 |
| Comparative Example 2 | $PdCl_2$—$CuCl_2$—$(NH_4)_{10}Mo_7O_{24}$/C | Pd/Cu/Mo =1:2:2.1 | 485 | 88 | 85 |

Note:
(*)₁ ... C = activated carbon carrier

Example 18

Production of Dimethyl Carbonate

The same solid catalyst as in Example 2 in an amount of 5 ml was place in a gas phase reaction tube having an inside diameter of 17 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 120° C.

A mixed gas consisting of 10% by volume of methyl nitrite, 10% by volume of carbon monoxide, 20% by volume of nitrogen monoxide, 9% by volume of methyl alcohol, 20 ppm by volume of hydrogen chloride and 57% by volume of nitrogen was fed into the reaction tube at a space velocity (GHSV) of 4,000 hr⁻¹.

In the reaction tube, the methyl nitrite reacted with carbon monoxide at a temperature of 120° C. under a pressure of 3 kg/cm²G in the presence of the solid catalyst.

The resultant reaction mixture was subjected to gas chromatographic analysis, and it was confirmed that at 4 hours after the start of the reaction procedure, the space time yield (STY) of dimethyl carbonate was 600 g/liter·hr, and at 10 hours after of the start of the reaction procedure, the space time yield (STY) was reduced to a level of 500 g/liter·hr. However, thereafter, the space time yield of dimethyl carbonate was maintained at the level of 500 g/liter·hr until the completion of the reaction, namely 100 hours after the start of the reaction. The selectivities (X and Y) of dimethyl carbonate based on carbon monoxide and on methyl nitrite were 97% and 98%, respectively, at 4 hours after the start of the reaction, and 95% and 96% at 10 hours after the start of the reaction, and thereafter, were maintained constant at the levels mentioned above.

Comparative Example 3

Preparation of Dimethyl Carbonate

The same preparation procedures and analysis for dimethyl carbonate as in Example 18 were carried out except that the same catalyst as in Comparative Example 1 was employed in an amount of 5 ml.

It was confirmed that the space time yield (STY) of dimethyl carbonate was at a level of 500 g/liter·hr at the stage of 4 hours after the start of the reaction, and reduced to a level of 400 g/liter·hr at the stage of 10 hours after the start of the reaction. Thereafter, the space time yield (STY) was maintained constant at the level of 400 g/liter·hr.

The selectivities of dimethyl carbonate were 88% based on carbon monoxide and 90% based on methyl nitrite at the stage of 4 hours after the start of the reaction, 83% based on carbon monoxide and 85% based on methyl nitrite at the stage of 10 hours after the start of the reaction, and thereafter were maintained constant at the above-mentioned levels, until the completion of the reaction.

Comparative Example 4

Preparation of Dimethyl Carbonate

The same preparation procedures and analysis for dimethyl carbonate as in Example 18 were carried out except that the same catalyst as in Comparative Example 1 was employed in an amount of 5 ml and no hydrogen chloride was employed.

It was confirmed that the space time yield (STY) of dimethyl carbonate was at a level of 500 g/liter·hr at the stage of 4 hours after the start of the reaction, and reduced to a level of 350 g/liter·hr at the stage of 10 hours after the start of the reaction, to 250 g/liter·hr at the stage of 20 hours after the start of the reaction, to a level of 150 g/liter·hr at the stage of 30 hours after the start of the reaction, and then to a level of 75 g/liter·hr at the stage of 50 hours after the start of the reaction.

The selectivities of dimethyl carbonate were 88% based on carbon monoxide and 89% based on methyl nitrite at the stage of 4 hours after the start of the reaction, 82% based on carbon monoxide and 84% based on methyl nitrite at the stage of 10 hours after the start of the reaction, 76% based on carbon monoxide and 78% based on methyl nitrite at the stage of 20 hours after the start of the reaction and then 60% based on carbon monoxide and 63% based on methyl nitrite at the stage of 50 hours after the start of the reaction.

Example 19

Preparation of Dimethyl Carbonate

The same preparation procedures and analysis for dimethyl carbonate as in Example 18 were carried out excepts that the same catalyst as in Example 14 was employed in an amount of 5 ml.

It was confirmed that the space time yield (STY) of dimethyl carbonate was at a level of 450 g/liter·hr at the stage of 4 hours after the start of the reaction, and reduced to a level of 350 g/liter·hr at the stage of 10 hours after the start of the reaction. Thereafter, the space time yield (STY) was maintained constant at the level of 350 g/liter·hr.

The selectivities of dimethyl carbonate were 98% based on carbon monoxide and 98% based on methyl nitrite at the stage of 4 hours after the start of the reaction, and 96% based on carbon monoxide and 96% based on methyl nitrite at the stage of 10 hours after the start of the reaction, and thereafter were maintained approximately constant at the above-mentioned levels, until the completion of the reaction.

Example 20 preparation of Catalyst

A catalyst was prepared by the same procedures as in Example 14 except that the granular activated carbon used as a carrier in Example 14 was replaced by y-alumina having a BET surface area of 190 m²/g.

The composition of the resultant catalyst was $PdCl_2CeCl_3/Al_2O_3$, the total amount of the metal compounds used as the catalyst components was 1.5% by weight in terms of metallic Pd, based on the weight of the carrier, and the atomic ratio of Pd to Ce was Pd:Ce=1:2.

Production of Dimethyl Carbonate

The above-mentioned solid catalyst in an amount of 2.5 ml was placed in a gas phase reaction tube having an inside diameter of 10 mm and equipped with an outside heating jacket. The reaction tube filled by the solid catalyst was fixed vertically and a heating medium consisting of a silicone oil was made to flow through the outside heating jacket to maintain the inside temperature of the reaction tube at a level of 100° C.

A mixed gas consisting of 25% by volume of methyl nitrite, 25% by volume of carbon monoxide, 2% by volume of nitrogen monoxide, 8% by volume of methyl alcohol 500 ppm by volume of hydrogen chloride and 40% by volume of nitrogen was fed into the reaction tube at a space velocity (GHSV) of 8,000 hr$^{-1}$ under the ambient atmospheric pressure.

In the reaction tube, the methyl nitrite reacted with carbon monoxide at a temperature of 100° C. under the ambient atmospheric pressure in the presence of the solid catalyst.

The resultant reaction mixture was subjected to gas chromatographic analysis, and it was confirmed that at the stage of 4 hours after the start of the reaction procedure, the space time yield (STY) of dimethyl carbonate was 880 g/liter·hr. This space time yield (STY) of 880 g/liter·hr was maintained unchanged until the stage of 50 hours after the start of the reaction, at which stage, the reaction was completed.

The selectivities (X and Y) of dimethyl carbonate was 98% based on carbon monoxide and 96% based on methyl nitrite at the stage of 4 hours after the start of the reaction, and were maintained approximately constant until the completion of the reaction.

Example 21

Preparation of Dimethyl Carbonate

The same preparation procedures and analysis for dimethyl carbonate as in Example 18 were carried out except that hydrogen chloride used in Example 18 was replaced by 100 ppm by volume of methyl chloroformate.

It was confirmed that the space time yield (STY) of dimethyl carbonate was at a level of 550 g/liter·hr at the stage of 4 hours after the start of the reaction. Thereafter, this space time yield (STY) of 550 g/liter·hr was maintained constant until the completion of the reaction, namely 100 hours after the start of the reaction.

Thee selectivities of dimethyl carbonate were 97% based on carbon monoxide and 98% based on methyl nitrite at the stage of 4 hours after the start of the reaction, and thereafter were maintained constant at the above-mentioned levels, until the completion of the reaction.

Comparative Example 5

Preparation of Dimethyl Carbonate

The same preparation procedures and analysis for dimethyl carbonate as in Example 21 were carried out except that the same catalyst as in Comparative Example 1 was employed in an amount of 5 ml.

It was confirmed that the space time yield (STY) of dimethyl carbonate was at a level of 500 g/liter·hr at the stage of 4 hours after the start of the reaction, and maintained constant at the level of 500 g/liter·hr until the completion of the reaction, namely 100 hours after the start of the reaction.

The selectivities of dimethyl carbonate were 88% based on carbon monoxide and 89% based on methyl nitrite at the stage of 4 hours after the start of the reaction, and thereafter were maintained approximately constant at the above-mentioned levels, until the completion of the reaction.

Example 22 preparation of Dimethyl Carbonate

The same preparation procedures and analysis for dimethyl carbonate as in Example 19 were carried out except that hydrogen chloride used in Example 19 was replaced by 100 ppm by volume of methyl chloroformate.

It was confirmed that the space time yield (STY) of dimethyl carbonate was at a level of 450 g/liter·hr at the stage of 4 hours after the start of the reaction, and thereafter was maintained at the level of 450 g/liter·hr until the completion of the reaction, namely 100 hours after the start of the reaction.

The selectivities of dimethyl carbonate were 98% based on carbon monoxide and 98% based on methyl nitrite at the stage of 4 hours after the start of the reaction, and thereafter were maintained approximately constant at the above-mentioned levels, until the completion of the reaction.

Example 23

Preparation of Dimethyl Carbonate

The same preparation procedures and analysis for dimethyl carbonate as in Example 20 were carried out except that hydrogen chloride used in Example 20 was replace by 500 ppm by volume of methyl chloroformate, and the reaction temperature was changed to 90° C.

It was confirmed that the space time yield (STY) of dimethyl carbonate was at a level of 880 g/liter·hr at the stage of 4 hours after the start of the reaction. Thereafter, the space time yield (STY) was maintained unchanged at the level of 880 g/liter·hr until the completion of the reaction, namely 50 hours after the start of the reaction.

The selectivities of dimethyl carbonate were 98% based on carbon monoxide and 96% based on methyl nitrite at the stage of 4 hours after the start of the reaction, and thereafter were maintained approximately constant at the above-mentioned levels, until the completion of the reaction.

The test results of Examples 18 to 23 and Comparative Examples 3 to 5 are shown in Table 2.

very high reaction rate with excellent selectivity and stability over a long period of time.

We claim:

1. A method of producing a carbonic acid diester, comprising the steps of:
   (A) catalytically reacting carbon monoxide with a nitrous acid ester in the presence of a solid catalyst composed of a solid carrier comprising at least one member selected from the group consisting of activated carbon, alumina and silica-alumina, and a catalytic solid material carried on the carrier and comprising:
      (1) a first catalyst component comprising at least one member selected from the group consisting of platinum group metals and compounds thereof;
      (2) a second catalyst component comprising at least one member selected from the group consisting of lanthanide group metals and compounds thereof; and
   (B) collecting the resultant carbonic acid diester from a reaction mixture discharged from the catalytic reaction step (A).

2. The method as claimed in claim 1, wherein the lanthanide group metal is selected from the group consisting of lanthanum, cerium, praseodymium, neodymium, promethium, samarium, europium, gadolinium terbium dysprosium, holmium, erbium, thulium, ytterbium, and lutetium.

3. The method as claimed in claim 1, wherein the lanthanide group metal compound is selected from the group consisting of oxides, halides and inorganic and

TABLE 2

| Example No. | Composition of catalyst Catalyst components/carrier | Catalytic activity reduction-inhibiting agent | Reaction time (hr) | | | | | | | | | | | |
|---|---|---|---|---|---|---|---|---|---|---|---|---|---|---|
| | | | 4 | 10 | 50 | 100 | 4 | 10 | 50 | 100 | 4 | 10 | 50 | 100 |
| | | | Space time yield (STY) (g/liter · hr) | | | | Selectivity (%) of dimethyl carbonate | | | | | | | |
| | | | | | | | Based on CO | | | | Based on methyl nitrite | | | |
| Example | | | | | | | | | | | | | | |
| 18 | PdCl$_2$—LaCl$_3$—CuCl$_2$/C | HCl | 600 | 500 | — | 500 | 97 | 95 | — | 95 | 98 | 96 | — | 96 |
| 19 | PdCl$_2$—CeCl$_3$/C | HCl | 450 | 350 | — | 350 | 98 | 96 | — | 96 | 98 | 96 | — | 96 |
| 20 | PdCl$_2$—CeCl$_3$/Al$_2$O$_3$ | HCl | 880 | — | 880 | — | 98 | — | 98 | — | 96 | — | 96 | — |
| 21 | PdCl$_2$—LaCl$_3$—CuCl$_2$/C | Methyl chloroformate | 550 | — | — | 550 | 97 | — | — | 97 | 98 | — | — | 98 |
| 22 | PdCl$_2$—CeCl$_3$/C | Methyl chloroformate | 450 | — | — | 450 | 98 | — | — | 98 | 98 | — | — | 98 |
| 23 | PdCl$_2$—CeCl$_3$/Al$_2$O$_3$ | Methyl chloroformate | 880 | — | 880 | — | 98 | — | 98 | — | 96 | — | 96 | — |
| Comparative Example | | | | | | | | | | | | | | |
| 3 | PdCl$_2$—CuCl$_2$/C | HCl | 500 | 400 | — | 400 | 88 | 83 | — | 83 | 90 | 85 | — | 85 |
| 4 | PdCl$_2$—CuCl$_2$/C | — | 500 | 350 | 75 | — | 88 | 82 | 60 | — | 89 | 84 | 63 | — |
| 5 | PdCl$_2$—CuCl$_2$/C | Methyl chloroformate | 500 | — | — | 500 | 88 | — | — | 88 | 89 | — | — | 89 |

Tables 1 and 2 clearly show that the method of the present invention in which a catalytic reaction of carbon monoxide with a nitrous acid ester is carried out in the presence of a specific catalyst containing catalytically active components, namely, platinum group metals or compound thereof and lanthanide group metals or compounds thereof, effectively eliminates the disadvantages of the conventional methods such that the reaction rate and selectivity of the desired compound are not always satisfactory and the conventional catalysts exhibit an unsatisfactory durability (catalyst life) for industrial use, and therefore a carbonic acid ester can be produced by the method of the present invention at a organic salts of the lanthanide group metals.

4. The method as claimed in claim 1, wherein the platinum group metal is selected from the group consisting of palladium, platinum, iridium, ruthenium and rhodium.

5. The method as claimed in claim 1, wherein the platinum group metal compound is selected from the group consisting of halides, nitrates, sulfates, phosphates, acetates, and benzoates of the palladium group metals.

6. The method as claimed in claim 1, wherein the catalytic solid material further comprises at least one additional component selected from the group consisting of iron, copper, bismuth, cobalt, nickel, tin, vanadium, molybdenum, tungsten and compounds of the above-mentioned metals.

7. The method as claimed in claim 6, wherein the additional component is selected from iron, copper, bismuth, cobalt, nickel, and tin and halides, inorganic acid salts, and organic acid salts of the above-mentioned metals.

8. The method as claimed in claim 6, wherein the additional catalyst component is present in an amount in terms of the metal, of 0.1 to 50 gram atom equivalents, per gram atom equivalent of the first catalyst component in terms of the platinum group metal.

9. The method as claimed in claim 1, wherein the catalytic solid material is deposited on the carrier by an impregnating, mix-kneading, depositing, evaporate-drying or coprecipitating method.

10. The method as claimed in claim 1, wherein the nitrous acid ester is selected from nitrites of lower aliphatic monohydric alcohols having 1 to 4 carbon atoms.

11. The method as claimed in claim 1, wherein the catalytic reaction of carbon monoxide with the nitrous acid ester is carried out at a temperature of 0° to 200° C.

12. The method as claimed in claim 1, wherein the catalytic reaction of carbon monoxide with the nitrous acid ester is carried out under a pressure of from the ambient atmospheric pressure to 20 kg/cm$^2$G.

13. The method as claimed in claim 1, wherein the catalytical reaction step (A) is carried out in a gas phase.

14. The method as claimed in claim 13, wherein, in the catalytic reaction step (A) in the gas phase, carbon monoxide is present in a concentration of 5 to 20% by volume, and the nitrous acid ester is present in a concentration of 20% by volume or less.

15. The method as claimed in claim 13, wherein, in the catalytic reaction step (A) in the gas phase, carbon monoxide is present in an amount of 0.1 to 10 moles per mole of the nitrous acid ester.

16. The method as claimed in claim 1, wherein the catalytic reaction of carbon monoxide with a nitrous acid ester is carried out in the presence of a catalytic activity reduction-inhibiting agent comprising at least one member selected from the group consisting of hydrogen chloride and chloroformic acid esters.

17. The method as claimed in claim 16, wherein hydrogen chloride is present in an amount of 1 to 50 molar % in term of the platinum group metal in the catalyst per unit time.

18. The method as claimed in claim 16, wherein the chloroformic acid ester is present in an amount of 1% by volume or less in the reaction mixture in the gas phase.

* * * * *